United States Patent [19]
Shigeta et al.

[11] Patent Number: 4,906,458
[45] Date of Patent: Mar. 6, 1990

[54] WATER-IN-OIL-TYPE COSMETIC

[75] Inventors: Akira Shigeta; Yuko Kikuta, both of Tokyo, Japan

[73] Assignee: Kao Corporation, Tokyo, Japan

[21] Appl. No.: 176,747

[22] Filed: Apr. 1, 1988

[30] Foreign Application Priority Data

Apr. 6, 1987 [JP] Japan .................................. 62-84471

[51] Int. Cl.$^4$ ........................ A61K 7/48; A61K 7/021
[52] U.S. Cl. ...................................... 424/63; 514/772
[58] Field of Search ................... 424/63; 514/844, 845, 514/937, 941, 772

[56] References Cited

U.S. PATENT DOCUMENTS

| 4,311,695 | 1/1982 | Starch ................................ 424/78 X |
| 4,675,179 | 6/1987 | Suzuki et al. .................... 514/991 X |
| 4,698,178 | 10/1987 | Hüttinger et al. ........ 252/DIG. 1 X |
| 4,782,095 | 11/1988 | Gum ................................ 514/941 X |

FOREIGN PATENT DOCUMENTS

| 152953 | 8/1985 | European Pat. Off. . |
| 154837 | 9/1985 | European Pat. Off. . |
| 176884 | 4/1986 | European Pat. Off. . |
| 271925 | 6/1988 | European Pat. Off. . |
| 204113 | 9/1986 | Japan . |
| 61-218509 | 9/1986 | Japan . |
| 2065687 | 7/1981 | United Kingdom . |

OTHER PUBLICATIONS

European search report for EP 88 10 5480.

Primary Examiner—Ellis P. Robinson
Assistant Examiner—Susan S. Rucker
Attorney, Agent, or Firm—Oblon, Spivak, McClelland, Maier & Neustadt

[57] ABSTRACT

A w/o-type emulsion cosmetic containing as its effective components, in a specific portion, (a) a specific type of dimethylpolysiloxanepolyoxyalkylene copolymer, (b) oil compounds, which contained at least one kind of polysiloxane, (c) a cosmetic powder of which the surface is treated to produce water-repellence, and (d) an aqueous solution of ethyl alcohol. The cosmetic is of a liquid or creamy type which produces a refreshing feeling upon wise, does not generate an oily, sticky feel, and prevents the make-up from breaking down by water or sweat. Thus, one of the advantageous application of the cosmetic as a liquid foundation for summer use.

2 Claims, No Drawings

WATER-IN-OIL-TYPE COSMETIC

BACKGROUND OF THE INVENTION

1. Field of the Invention

This invention relates to a water-in-oil-type cosmetic and, more particularly, to a water-in-oil-type make-up cosmetic, which possesses an excellent emulsion stability, imparts a refreshing feeling to the skin upon application, and can be well retained on the skin after application.

2. Description of the Background Invention

Foundations, eye liners, mascaras, and the like are included in emulsion-type cosmetics for make-up use. They are classified into oil-in-water-type cosmetics (hereinafter referred to as "o/w type cosmetics") and water-in-oil-type cosmetics (hereinafter referred to as "w/p-type cosmetics") depending on the type of emulsion employed.

As compared with oil-based cosmetics, these emulsion-type cosmetics impact a sense of refreshment and are less oily when applied to the skin because water is incorporated as their component. Additional features of the emulsion-type cosmetics are that they are prepared mostly in liquid or cream form and are well extendible on the skin, providing an evenly finished make-up.

In particular, as compared with o/w type cosmetics, w/o-type cosmetics, being of a continuous oil phase, have a higher resistance to bacteria, form an oil film with a low water-permeability on the skin, which can protect the skin from becoming dry over a long period of time and does not re-emulsify when the same comes into contact with water on such occasions as swimming, washing, kitchen work, or sweating, thus preventing the make-up from running, cracking or becoming spottedly discolored.

It has conventionally been difficult to formulate a stable w/o-type emulsion. In order to make a stable emulsion, it is sometimes necessary to restrict the amount of water to be incorporated in the dispersion phase or to employ an oil component with a higher viscosity for the continuous phase. This brings about drawbacks in which the cosmetics produce a stickiness or strong oily feeling upon use.

For providing an emulsion cosmetic with better capability to refresh the user upon use, it is imperative that the cosmetic contain a smaller amount of low viscosity oil components.

Polysiloxanes (hereinafter sometimes referred to as "silicone oils") of formulae (II), (III) and (IV) hereinafter described are suitable oil components for cosmetics since they are capable of forming a thin, homogeneous film on the skin and imparting a less sticky, smoother feeling. These silicone oils, however, are insufficiently compatible with commonly used surface active agents and other oil components. Furthermore, they are not readily emulsifiable so that it is very difficult to obtain a fine homogeneous, emulsion from them.

Another effective way of providing a cosmetic with good refreshing capability upon use is to incorporate ethyl alcohol in it. Addition of ethyl alcohol to an emulsion, however, greatly impairs the stability of the emulsion system.

Because of these reasons, the wide, popular use of w/o-type cosmetics is restricted in spite of their advantages over o/w-type cosmetics. Therefore, development of w/o-type cosmetics featuring higher stability and the provision of a better, more refreshing feeling upon use has long been desired.

In light of this background, the present inventors have conducted extensive studies for overcoming the above-mentioned problems in preparing w/o-type cosmetics. As a result, the inventors found that a highly stable w/o-type cosmetic which gives a fine refreshing feeling upon use, and which can be well retained on the skin after application, can be prepared by using a specific type of dimethylpolysiloxanepolyoxyalkylene copolymer as an emulsifier; by providing an oil phase comprising a silicone oil and a cosmetic powder the surface of which is treated to make the same water-repellent; and by adding to this oil phase a water phase containing a specified proportion of ethyl alcohol. These findings have led to the completion of this invention.

SUMMARY OF THE INVENTION

Accordingly, an object of this invention is to provide a water-in-oil-type cosmetic comprising as its effective components:

(a) 0.05–5% by weight of a dimethylpolysiloxanepolyoxyalkylene copolymer represented by the following general formula (I):

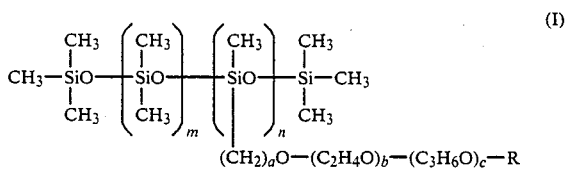

in which a is a value of 1–5, b is a value of 7–15, c is a value of 0–4, m is a value of 20–100, n is a value of 1–5, and R represents a hydrogen atom or an alkyl group having 1–5 carbon atoms;

(b) 7–60% by weight of oil components, wherein not less than 60% by weight of at least one kind of polysiloxane represented by the following formulae, (II), (III), or (IV), is contained:

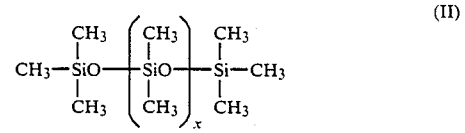

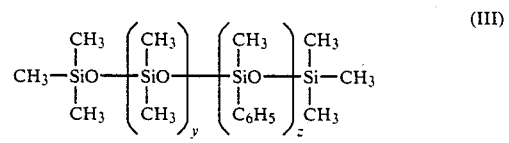

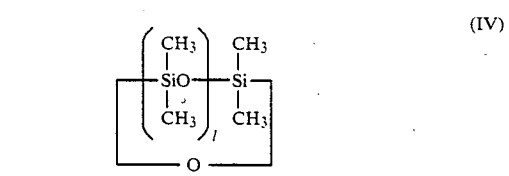

in which x is a value of 1–100, z is a value of not less than 1, y+z is a value of 1–100, and $\iota$ is a value of 2–6;

(c) 3–60% by weight of a cosmetic powder of which the surface is treated to provide water-repellence; and (d) 15–80% by weight of an aqueous solution of ethyl alcohol, wherein the proportion by weight of ethyl alcohol/water is 50/50-2/98.

Other objects, features, and advantages of this invention will be more fully understood by the following detailed description and preferred embodiments of the invention.

DETAILED DESCRIPTION OF THE INVENTION AND PREFERRED EMBODIMENTS

The dimethylpolysiloxanepolyoxyalkylene copolymer, component (a) of the w/o-type emulsion cosmetic of this invention is insoluble in water. When water-soluble dimethylpolysiloxanepolyoxyalkylene copolymer is used, the resulting emulsion tends to have larger emulsion particles. This renders the product less stable, causing separation of the water phase components during storage over a prolonged period of time. In addition, since a water soluble dimethylpolysiloxanepolyoxyalkylene is hydrophilic itself, when the w/o-type emulsion cosmetic containing the same comes into contact with water or sweat, the w/o-type emulsion cosmetic tends to re-emulsify, which may lead to breaking or cracking of the make-up.

Desirable examples of component (a) are those dimethylpolysiloxanepolyoxyalkylenes of formula (I), and particularly those when R in formula (I) is a hydrogen atom, a is 3, b is 7–15, c is 0, m is 20–100, more desirably 50–100, and n is 1–5. One example of such dimethylpolysiloxanepolyoxyalkylene which can be readily available is Toray Silicone SH 3775C manufactured by Toray Silicone Co., Ltd.

This component (a) is formulated in the w/o-type emulsion cosmetic of this invention in an amount of 0.05–5% by weight (hereinafter referred to simply as "%"), and preferably 0.1–2%. Formulating this component in excess of 5% does not produce any enhanced effect, and will thus bring about no better economy. On the other hand, if the amount is less than 0.05%, adverse effect is exhibited by this component, giving a product with poor prolonged stability.

Component (b) of the w/o-type emulsion cosmetic according to the present invention is comprised of at least 60% polysiloxane and less than 40% other oil components. Among the polysiloxanes, preferred are those having an $\iota$-value of between 3 and 5 in formula (IV). Since these polysiloxanes are volatile, they are not retained on the skin when used as a cosmetic component, enabling them to impart a refreshing feeling to the skin free of stickiness or oiliness. In addition, these polysiloxanes are more stable over a prolonged period of time than polysiloxanes represented by formulae (II) or (III). Specific examples of these polysiloxanes readily available on the market are SH244, SH344, SC245, and DC345 (Trade names; manufactured by Toray Silicone Co., Ltd.), KF994, KF995, KF996, and KF9956 (Trade names; manufactured by Shinetsu Kagaku Kogyo Co., Ltd.), and TSF404, TSF405, and TSF406 (Trade names; manufactured by Toshiba Silicone Co., Ltd.).

Given as examples of oil components other than polysiloxanes of component (b) of this invention are hydrocarbons such as liquid paraffin and squalane, oils and fats derived from animals or vegetables such as olive oil and jojoba oil, synthetic esters such as octyldodecyl myristate, isopropyl palmitate, isopropyl myristate, and the like.

When less than 60% polysiloxanes are formulated in this component (b), the emulsion particles tend to be larger and it is difficult to maintain the product for a long period of time.

Component (b) is formulated in the w/o-type emulsion cosmetic of this invention in an amount of 7–60%, preferably 15–40%. When the proportion is less than 7%, the emulsion obtained is less stable. On the other hand, if the proportion is more than 60%, the refreshing feeling imparted by the water phase components is impaired.

Component (c) of the w/o-type emulsion cosmetic of this invention is a cosmetic powder surface of which is treated so as to make it water-repellent. The cosmetic powder may be any organic or inorganic powdery material commonly used for cosmetics, and includes, for example, extenders such as talc, cericite, mica, kaolin, silica, nylon powder, polyethylene powder, silk powder, or cellulose powder; pigments or coloring materials such as titanium oxide, iron oxide, zince oxide, ultramarine blue, iron blue, chromium oxide, coloring agents derived from organic tars, and lakes; or composites pigments such as titanium-mica, iron oxide coated-mica, or the like. Examples of water-repellence donating reagents are silicones, higher fatty acids, higher alcohols, fatty acid esters, metallic soaps, amino acids, alkyl phosphates, fluoroalkyl surfactants, fluoroalkyl polymers, and the like.

The method of treating the surface of a cosmetic powder may be a conventional one. Typically, (i) the water-repellence donating reagent is dissolved in an organic solvent such as hexane, toluene, benzene, or the like, (ii) a cosmetic powder is then added to this solution, and (iii) the organic solvent is removed from the mixture by evaporation or other suitable means. The amount of the water-repellence donating reagent may be 0.5–20% by weight, and preferably 1–10% by weight, in the treated powder.

A preferred example of component (c) is a cosmetic powder obtained by treating its surface with silicone. This type of cosmetic powder has the strongest water-repellence, and can effectively prevent the make-up from breaking down when applied to an emulsion cosmetic. In addition, the emulsion is dense and fine, and exhibits excellent stability for a long period of time. Although a cosmetic powder without being treated by a water-repelling reagent can provide relatively stable emulsions, make-up produced using such cosmetics is very liable to break down by water or sweat due to hydrophilic nature of the surface of the cosmetic powder.

This component (c) is formulated in the w/o-type emulsion cosmetic of this invention in an amount of 3–60%, preferably 7–30%. If the proportion is less than 3%, the composition cannot exhibit an adequate coloring effect required for a cosmetic intended for make-up purpose. Formulation in excess of 60%, on the other hand, makes the cosmetic too powdery and diminishes its refreshment capability which is the purpose of this invention.

It is essential for the w/o-type emulsion cosmetic of this invention that the ratio of ethyl alcohol/water of component (d) be in the range of 50/50–2/98, and preferably 35/35–5/95. A sufficient refreshing feeling cannot be obtained with an ethyl alcohol/water ratio smaller than 2/98. If the ratio is larger than 50/50, the stability of the emulsion is impaired, and the composition obtained gives a strong stimulus to the skin.

This component (d) is formulated in the w/o-type emulsion cosmetic of this inventin is an amount of 15-80%, and preferably 30-70%. If the proportion is less than 15%, the refreshing effect when applied to the skin is insufficient. Formulation of this component in excess of 80% impairs the long-range stability of the product.

Various ingredients may be formulated in component (d) as required. These may be humectants, including glycerol, sorbitol, maltitol, propylene glycol, dipropylene glycol, 1,3-butylene glycol, sodium pyrrolidone carboxylate, polyoxyethylenemethyl glucoside, polyoxypropylenemethyl glucoside, glucose, and the like; amino acids such as glycine, serine, and proline; and other agents with pharmaceutical effects such as antiphlogistics, antiseptics, vitamins, and the like.

Preparation of the w/o-type emulsion cosmetic according to this invention may, for instance, be carried out as follows.

Component (a) is first added to component (b) and the mixture is stirred to disperse the former in the latter. To this mixture is added component (c), and then component (d) is added a bit at a time while stirring to obtain the target w/o-type emulsion cosmetic. This procedure may be carried out at a temperature in the range of 5°–90° C., with the w/o-type emulsion cosmetic featuring excellent stability capable of being prepared at any temperature in this range.

One of the outstanding features of the w/o-type emulsion cosmetic of this invention thus prepared is in the state of the emulsion particles. When the particles are examined by microscope, the normally observed state is that in which the particles of the cosmetic powders adhere to the surface of the water-phase particles having diameters of 10–50 μm. If such particles of cosmetic powders exist inside the water-phase particles, such emulsions cannot remain stable for a long period of time. Another feature of the emulsion is that although the emulsion particles are very stable while the product is shaken or left to stand, they readily separate if coated to form a thin film and some slight shear is applied to it. This is evidenced by the fact that the same phenomenon takes place when the cosmetic is applied to the skin. More specifically, it is presumed that although the cosmetic is in fact a water-in-oil-type emulsion, the emulsion is broken down upon application to the skin, allowing the water phase components including ethyl alcohol to come into contact with the skin, bringing about a refreshing feeling to users.

It is desirable that the w/o-type emulsion cosmetic of this invention have a low viscosity. If the viscosity is high, it cannot provide a refreshing feeling both in terms of appearance and actual application.

During storage over a long period of time, a small amount of oil phase components may separate and form a layer on top of the composition. Such a product can be used as a shake-type cosmetic if its viscosity is small enough to make the composition homogeneous by slightly shaking the same.

The w/o-type emulsion cosmetic of this invention is a liquid or creamy cosmetic which produces a refreshing feeling upon use, does not generate an oily, sticky feel, and prevents the make-up from breaking down by water or sweat.

There is no special limitation to the specific application of the w/o-type emulsion cosmetic according to this invention, so long as such an application is directed to make-up cosmetics containing a cosmetic powder. A typical example of the application for making the best use of the advantageous features of this w/o-type emulsion cosmetic, i.e., providing a highly satisfactory refreshing feeling and preventing the make-up from cracking or breaking down, is as a foundation. When the w/o-type emulsion cosmetic of this invention is realized as being a liquid possessing the above-mentioned features, a particularly advantageous application for the product is as a liquid foundation for summer use.

Well known as liquid foundations for use in summer are those of the suspension type wherein an untreated cosmetic powder is suspended in a water phase containing ethanol. The untreated cosmetic powder of such a suspension type-foundation sedimentates, and the water phase separates when the foundation is left to stand. Moreover, a critical drawback of this type of liquid foundation is that it tends to cause the breaking or cracking of make-up due to exposure to water or sweat.

The w/o-type emulsion cosmetic of this invention overcomes such this disadvantage.

Other features of the invention will become apparent in the course of the following description of the exemplary embodiments which are given for illustration of the invention and are not intended to be limiting thereof.

EXAMPLES

Example 1

Liquid foundations having formulations shown in Table 1 were prepared according to the following method and their emulsion stability was examined. The results emulsion stability testing are given in Table 2.

Preparation

Powder and oil phase components were mixed and stirred to disperse the powder in oil, and heated to raise the temperature to 40° C. To this mixture, the water phase components the temperature of which was controlled at 40° C. were added while stirring to emulsify the entire mixture. The emulsion was transferred to a glass container and left to cool at room temperature.

Formulation

TABLE 1

| | Composition (%) | | | | | | | | |
|---|---|---|---|---|---|---|---|---|---|
| | Invented Products | | | Comparative Products | | | | | |
| Components | A | B | C | D | E | F | G | H | I |
| Oil phase | | | | | | | | | |
| Dimethylpolysiloxane-polyoxyalkylene copolymer (water-soluble)* | — | — | — | — | 0.5 | — | — | — | — |
| Dimethylpolysiloxane-polyoxyalkylene copolymer (water-insoluble)** | 0.5 | 0.5 | 0.5 | 0.02 | — | 0.5 | 0.5 | 0.5 | 0.5 |
| Octamethylcyclotetrasiloxane (SH244 manufactured | 15 | 15 | — | 15 | 15 | 6 | 4 | 15 | 4 |

TABLE 1-continued

| | | | | | | | | | |
|---|---|---|---|---|---|---|---|---|---|
| by Toray Silicone Co., Ltd.) | | | | | | | | | |
| Decamethylcyclopenta-siloxane (SH245 manufactured by Toray Silicone Co., Ltd.) | 5 | 5 | — | 5 | 5 | 4 | 1 | 5 | 3 |
| Dimethylpolysiloxane (SH200 (20 CS) manufactured by Toray Silicone Co., Ltd.) | 10 | 5 | 30 | 10 | 10 | — | — | 10 | 3 |
| Jojoba oil | — | 5 | — | — | — | 20 | — | — | — |
| Perfume | Small amount | Small amount | Small amount | Small amount | Small amount | Small amount | Small amount | Small amount | Small amount |
| Powdery substance | | | | | | | | | |
| Silicone-treated cosmetic powder*** | 15 | 15 | 15 | 15 | 15 | 15 | 20 | 15 | 5 |
| Water phase | | | | | | | | | |
| Ethyl alcohol/water (20/80 by weight) | Balance | Balance | Balance | Balance | Balance | Balance | Balance | — | Balance |
| Ethyl alcohol/water (60/40 by weight) | — | — | — | — | — | — | — | Balance | — |

*SH 3771 (manufactured by Toray Silicone Co., Ltd.); a compound of Formula (I), in which m = 3–10, n = 1–5, a = 10–17, b = 0, c = 0, and R = H
**A compound of Formula (I); m = 50–100, n = 1–5, a = 3, b = 7–15, c = 0, and R = H
***A silicone-treated cosmetic powder prepared by adding 2% methylhydrogenepolysiloxane (KF 99, manufactured by Sinetsu Kagaku Kogyo Co., Ltd.) to a raw cosmetic powder of the following composition (raw cosmetic powder) and heat-treating the same.

Titanium oxide   8 parts by weight
Talc             4 parts by weight
Red iron oxide   1.2 parts by weight
Yellow iron oxide 2.6 parts by weight
Black ion oxide  0.2 parts by weight Results

TABLE 2

| | State of emulsion | Stability after one-month storage | |
|---|---|---|---|
| Invented Products | | | |
| A | Good (w/o) | at 40° C. | (No change) |
| | | at 5° C. | (No change) |
| B | Good (w/o) | at 40° C. | (No change) |
| | | at 5° C. | (No change) |
| C | Good (w/o) | at 40° C. | (No change) |
| | | at 5° C. | (No change) |
| Comparative Products | | | |
| D | Rather poor (w/o) | at 40° C. | (Separated) |
| | | at 5° C. | (Separated slightly) |
| E | Rather poor (w/o) | at 40° C. | (Separated) |
| | | at 5° C. | (Separated) |
| F | Separated immediately after preparation | | |
| G | Rather poor (w/o) | at 40° C. | (Separated) |
| | | at 5° C. | (Separated slightly) |
| H | Rather poor (w/o) | at 40° C. | (Separated) |
| | | at 5° C. | (Separated slightly) |
| I | Rather bad (w/o) | at 40° C. | (Separated) |
| | | at 5° C. | (Separated) |

As is evident from Table 2, the w/o-type emulsion cosmetics of this invention exhibites good emulsion stability.

Example 2

Foundations having formulations shown in Table 3 were prepared according to the method described in Example 1, and subjected to organoleptic evaluation by 10 female panelists as to their physical appearance and the degree of satisfaction upon use. The results are given in Table 4, in which the following standard is applicable with respect to the results of organoleptic evaluation:

AAA: At least 8 out of 10 panelists indicated their satisfaction upon use of the tested product;
BBB: At least 6 out of 10 panelists indicated their satisfaction upon use of the tested product;
CCC: At least 4 out of 10 panelists indicated their satisfaction upon use of the tested product;
DDD: less than 4 out of 10 panelists indicated their satisfaction upon use of the tested product.

Formulation

TABLE 3

| | Composition (%) | | | | | | | |
|---|---|---|---|---|---|---|---|---|
| | Invented Products | | | | Comparative Products | | | |
| Components | J | K | L | M | N | O | P | Q |
| Oil phase | | | | | | | | |
| Dimethylpolysiloxane-polyoxyalkylene copolymer (water-insoluble)* | 0.4 | 0.4 | 0.4 | 0.4 | 0.4 | 0.4 | 0.4 | 0.4 |
| Octamethylcyclotetra-siloxane (SH244 manufactured by Toray Silicone Co., Ltd.) | 16 | 4 | 35 | 16 | 16 | 44 | 13 | 30 |
| Decamethylcyclopenta-siloxane (SH245 manufactured by Toray Silicone Co., Ltd.) | 4 | 1 | 10 | 4 | 4 | 11 | 2 | 10 |
| Methylphenylpolysiloxane (KF56 manufactured by Shinetsu Kagaku Co., Ltd.) | 10 | 25 | 10 | 10 | 10 | 10 | 2 | 10 |
| Perfume | Small amount | Small amount | Small amount | Small amount | Small amount | Small amount | Small amount | Small amount |

TABLE 3-continued

| | Composition (%) | | | | | | | |
|---|---|---|---|---|---|---|---|---|
| | Invented Products | | | | Comparative Products | | | |
| Components | J | K | L | M | N | O | P | Q |
| Powdery Substance | | | | | | | | |
| Silicone-treated cosmetic powder* | 12 | 12 | 20 | 50 | 12 | 12 | 63 | 40 |
| Water phase | | | | | | | | |
| Ethyl alcohol/water (0/100 by weight) | — | — | — | — | Balance | — | — | — |
| Ethyl alcohol/water (5/95 by weight) | — | Balance | — | — | — | — | — | — |
| Ethyl alcohol/water (20/80 by weight) | Balance | — | — | — | — | — | — | — |
| Ethyl alcohol/water (45/55 by weight) | — | — | Balance | Balance | — | Balance | Balance | Balance |

*The same materials as those used in Example 1

Results
TABLE 4

| | Evaluation Results | | | |
|---|---|---|---|---|
| | Refreshing Feeling | Oily-like Feel | Too Powdery | Physical Appearance |
| Invented Products | | | | |
| J | AAA | AAA | AAA | AAA |
| K | AAA | BBB | AAA | AAA |
| L | AAA | BBB | AAA | AAA |
| M | BBB | AAA | BBB | AAA |
| Comparative Products | | | | |
| N | DDD | AAA | AAA | AAA |
| O | CCC | CCC | AAA | AAA |
| P | CCC | AAA | DDD | AAA |
| Q | DDD | BBB | BBB | AAA |

As is evident from Table 4, the invented products provided more a refreshing feeling, less oily-like feel, and a less powdery feeling than the comparative products.

Example 3

Liquid foundations having formulations shown in Table 5 were prepared according to the method described in Example 1, and subjected to organoleptic evaluation by 10 female panelists as to their physical appearance, degree of satisfaction upon use, water resistance, and sweat resistance. The results are presented in Table 6, in which the same standard as described in Example 2 was applicable with respect to the organoleptic evaluation results.

Formulation
TABLE 5

| | Composition (%) | | | | | |
|---|---|---|---|---|---|---|
| | Invented Products | | | Comparative Products | | |
| Components | R | S | T | U | V | W |
| Oil phase | | | | | | |
| Dimethylpolysiloxane-polyoxyalkylene copolymer (SH3746 manufactured by Toray Silicone Co., Ltd. (water-soluble) | — | — | — | 0.3 | 1 | — |
| Dimethylpolysiloxane-polyoxyalkylene copolymer (water-insoluble)* | 1 | 1 | 1 | — | — | 1 |
| Decamethylcyclopenta-siloxane (SH245 manufactured by Toray Silicone Co., Ltd.) | 20 | 20 | 20 | 20 | 20 | 20 |
| Methylphenylpolysiloxane (SH556 manufactured by Toray Silicone Co., Ltd.) | 7 | 7 | 7 | 7 | 7 | 7 |
| Perfume | small amount | small amount | small amount | small amount | small amount | small amount |
| Powdery substance** | | | | | | |
| Untreated cosmetic powder | — | — | — | — | — | 10 |
| Cosmetic powder treated with myristic acid | 10 | — | — | — | — | — |
| Cosmetic powder treated with alkyl phosphate | — | 10 | — | — | — | — |
| Silicone-treated cosmetic powder | — | — | 10 | 10 | 10 | — |
| Water phase | | | | | | |
| Ethyl alcohol/water | balance | balance | balance | balance | balance | balance |

TABLE 5-continued

| | Composition (%) | | | | | |
|---|---|---|---|---|---|---|
| | Invented Products | | | Comparative Products | | |
| Componenets | R | S | T | U | V | W |
| (20/80 by weight) | | | | | | |

*The same material as used in Example 1
**The following cosmetic powders were used:
Untreated cosmetic powder The same raw cosmetic powder used as the raw material in Example 1
Cosmetic powder treated with myristic acid The same raw cosmetic powder used in Example 1 was added to aluminum myristate in an amount of 2% by weight of the treated powder in hexane. The resulting mixture was mixed and hexane was removed by evaporation.
Alkylphosphate-treated cosmetic powder The same raw cosmetic powder used in Example 1 was added to dicetyl phosphate in an amount of 2% by wieght of the treated powder in hexane. The resulting mixture was mixed and hexane was removed by evaporation.
Silicone-treated cosmetic powder The same silicone-treated cosmetic powder as that used in Example 1

Results

TABLE 6

| | Evaluation Results | | | |
|---|---|---|---|---|
| | Physical Appearance | Feeling upon use | Water* Resistance | Sweat** Resistance |
| Invented Products | | | | |
| R | AAA | AAA | AAA | AAA |
| S | AAA | AAA | AAA | AAA |
| T | AAA | AAA | AAA | AAA |
| Comparative Products | | | | |
| U | CCC | CCC | CCC | CCC |
| V | BBB | BBB | DDD | DDD |
| W | AAA | BBB | DDD | DDD |

*Water resistance: The skin to which the foundation was applied was exposed to flowing water for a prescribed period of time, and the make-up break down or cracking conditions were observed.
**Sweat resistance: The subjects using the foundation stayed in a room having a constant temperature of 40° C. and a humidity of 80% for 1 hour, and the make-up break down or cracking conditions were observed.

As shown in Table 6, the cosmetics according to this invention present a good physical appearance and provide satisfaction on use. In addition, they exhibit superior water and sweat resistances so that the make-up produced using them is less liable to be decomposed.

Example 4

Eye liner:

Formulation

| | | |
|---|---|---|
| i. | Silicone-treated black iron oxide* | 20% |
| ii. | Dimethylpolysiloxanepolyoxyalkylene copolymer (water-insoluble)** | 0.8% |
| iii. | Octamethylcyclotetrasiloxane** | 22.2% |
| iv. | Dimethylpolysiloxane** | 5% |
| v. | Jojoba oil | 2% |
| vi. | 2% aqueous ethanol | 50% |

*Powdery black iron oxide treated by silicone in the same manner as described in Example 1.
**The same materials as used in Example 1

Preparation

To the mixture of components iii, iv, and v above, component ii was added while stirring, followed by addirion of i with continued stirring until dispersed and heated to 40° C., to which component vi was slowly added while stirring to obtain an eye liner.

Example 5

Mascara:

Formulation

| | | |
|---|---|---|
| i. | Silicone-treated black iron oxide* | 15% |
| ii. | Silicone-treated cericite* | 4% |
| iii. | Silicone-treated kaolin* | 2% |
| iv. | Dimethylpolysiloxanepolyoxyalkylene copolymer (water-insoluble)** | 0.6% |
| v. | Octamethylcyclotetrasiloxane** | 3% |
| vi. | Decamethylcyclopentasiloxane** | 3% |
| vii. | Methyphenylpolysiloxane*** | 4% |
| viii. | 2% aqueous ethanol | Balance |
| ix. | Antiseptic | 0.4% |

*Powdery black iron oxide, cericite or kaolin treated with silicone in the same manner as described in Example 1
**The same materials as used in Example 1
***The same material as used in Example 2

Preparation

To the mixture of components iv, v, vi, and vii above, components i, ii, and iii, which were homogeneously mixed, were added while stirring until dispersed and heated to 40° C., to which component viii followed by component ix were slowly added while stirring to obtain a mascara.

Example 6

Eye shadow:

Formulation

| | | |
|---|---|---|
| i. | Silicone-treated talc* | 5.6% |
| ii. | Silicone-treated cericite* | 10% |
| iii. | Silicone-treated titanium mica* | 12% |
| iv. | Silicone-treated ultramarine blue* | 1.7% |
| v. | Silicone-treated black iron oxide* | 0.7% |
| vi. | Dimethylpolysiloxanepolyoxyalkylene copolymer (water-insoluble)** | 0.3% |
| vii. | Octamethylcyclotetrasiloxane** | 5% |
| viii. | Decamethylcyclopentasiloxane** | 10% |
| ix. | Dimethylpolysiloxane** | 5% |
| x. | Perfume | Small amount |
| xi. | 5% aqueous ethanol | Balance |

*Powdery talc, cericite, titanium mica, ultramarine blue, and black iron oxide treated by silicone in the same manner as described in Example 1.
**The same materials as used in Example 1

Preparation

To the mixture of components vii, viii, and ix above, component vi was added while stirring, followed by addition of components i–v, which were homogeneously mixed, with continued stirring until dispersed and heated to 40° C., to which component xi was slowly added while stirring. After the mixture was cooled, component x was added to obtain an eye shadow.

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent is:

1. A water-in-oil-type cosmetic comprising as its effective components:
   (a) 0.05–5% by weight of a water-insoluble dimethylpolysiloxanepolyoxyalkylene copolymer represented by the following general formula (I):

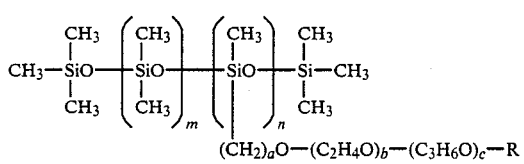

$$\text{(CH}_2)_a\text{O}-(\text{C}_2\text{H}_4\text{O})_b-(\text{C}_3\text{H}_6\text{O})_c-\text{R} \qquad \text{(I)}$$

in which a is a value of 1–5, b is a value of 7–15, c is a value of 0–4, m is a value of 20–100, n is a value of 1–5, and R represents a hydrogen atom or an alkyl group having 1–5 carbon atoms;

(b) 7–60% by weight of oil components, wherein not less than 60% by weight of at least one kind of polysiloxane represented by the following formulae, (II), (III) or (IV), is contained:

$$\text{CH}_3-\underset{\underset{\text{CH}_3}{|}}{\overset{\overset{\text{CH}_3}{|}}{\text{SiO}}}-\left(\underset{\underset{\text{CH}_3}{|}}{\overset{\overset{\text{CH}_3}{|}}{\text{SiO}}}\right)_x-\underset{\underset{\text{CH}_3}{|}}{\overset{\overset{\text{CH}_3}{|}}{\text{Si}}}-\text{CH}_3 \qquad \text{(II)}$$

$$\text{CH}_3-\underset{\underset{\text{CH}_3}{|}}{\overset{\overset{\text{CH}_3}{|}}{\text{SiO}}}-\left(\underset{\underset{\text{CH}_3}{|}}{\overset{\overset{\text{CH}_3}{|}}{\text{SiO}}}\right)_y-\left(\underset{\underset{\text{C}_6\text{H}_5}{|}}{\overset{\overset{\text{CH}_3}{|}}{\text{SiO}}}\right)_z-\underset{\underset{\text{CH}_3}{|}}{\overset{\overset{\text{CH}_3}{|}}{\text{Si}}}-\text{CH}_3 \qquad \text{(III)}$$

$$\left[\left(\underset{\underset{\text{CH}_3}{|}}{\overset{\overset{\text{CH}_3}{|}}{\text{SiO}}}\right)_l-\underset{\underset{\text{CH}_3}{|}}{\overset{\overset{\text{CH}_3}{|}}{\text{Si}}}-\text{O}\right] \qquad \text{(IV)}$$

in which x is a value of 1–100, z is a value of not less than 1, y+z is a value of 1–100, and l is a value of 2–6;

(c) 3–60% by weight of a cosmetic powder of which the surface is treated to produce water-repellence; and (d) 15–80% by weight of an aqueous solution of ethyl alcohol, wherein the proportion by weight of ethyl alcohol/water is 50/50–2/98.

2. The water-in-oil-type cosmetic as claimed in claim 1, wherein component (c) is a cosmetic powder the surface of which is treated by a water-repellent donating agent selected from a member consisting of higher fatty acids, silicones, and alkyl phosphates.

* * * * *